United States Patent
Mukaide et al.

(10) Patent No.: US 9,031,189 B2
(45) Date of Patent: May 12, 2015

(54) X-RAY IMAGING APPARATUS AND X-RAY IMAGING METHOD

(75) Inventors: Taihei Mukaide, Yokohama (JP); Takashi Noma, Hadano (JP); Kazunori Fukuda, Fujisawa (JP); Masatoshi Watanabe, Isehara (JP); Kazuhiro Takada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 484 days.

(21) Appl. No.: 13/522,474

(22) PCT Filed: Jan. 27, 2011

(86) PCT No.: PCT/JP2011/052203
§ 371 (c)(1),
(2), (4) Date: Jul. 16, 2012

(87) PCT Pub. No.: WO2011/093523
PCT Pub. Date: Aug. 4, 2011

(65) Prior Publication Data
US 2012/0294421 A1    Nov. 22, 2012

(30) Foreign Application Priority Data

Jan. 29, 2010  (JP) ................... 2010-019448
Jul. 14, 2010  (JP) ................... 2010-159886

(51) Int. Cl.
*G01N 23/04* (2006.01)
*G01T 1/29* (2006.01)

(52) U.S. Cl.
CPC . *G01T 1/29* (2013.01); *G01N 23/04* (2013.01)

(58) Field of Classification Search
CPC ........ A61B 6/484; A61B 6/032; G01N 23/06; G21K 2207/005; G21K 1/10
USPC .......................... 378/53, 62; 702/28, 172, 189
See application file for complete search history.

(56) References Cited

U.S. PATENT DOCUMENTS 5,812,629 A    9/1998  Clauser
8,214,158 B2 *  7/2012  Mukaide et al. ............... 702/28
(Continued)

FOREIGN PATENT DOCUMENTS

CN    101011251 A    8/2007
JP    2007203062 A    8/2007
(Continued)

OTHER PUBLICATIONS

Kagoshima et al.;"Scanning Differential-Phase-Contrast Hard X-Ray Microscopy with Wedge Absorber Detector", Japanese Journal of Applied Physics, No. 11A, 2004, pp. L 1449-L 1451, vol. 43.

*Primary Examiner* — Michael Maskell
(74) *Attorney, Agent, or Firm* — Canon USA Inc. IP Division

(57) ABSTRACT

An X-ray imaging apparatus acquiring a differential phase contrast image of a test object without using a light-shielding mask for X-ray. The apparatus includes an X-ray source, a splitting element configured to spatially divide an X-ray emitted from an X-ray source and a scintillator configured to emit light when a divided X-ray beam divided at the splitting element is incident on the scintillator. The apparatus also includes a light-transmission limiting unit configured to limit transmitting amount of the light emitted from the scintillator and a plurality of light detectors each configured to detect the amount of light that has transmitted through the light-transmission limiting unit. The light-transmission limiting unit is configured such that a light intensity detected at each of the light detectors changes in response to a change in an incident position of the X-ray beam.

16 Claims, 13 Drawing Sheets

(56) References Cited

U.S. PATENT DOCUMENTS

| | | |
|---|---|---|
| 2005/0286680 A1 | 12/2005 | Momose |
| 2007/0064868 A1* | 3/2007 | Kostka et al. .................. 378/53 |
| 2007/0183580 A1 | 8/2007 | Popescu et al. |
| 2010/0189218 A1* | 7/2010 | Sakaguchi et al. ............. 378/62 |
| 2010/0318302 A1* | 12/2010 | Mukaide et al. ................ 702/28 |
| 2011/0158389 A1* | 6/2011 | Mukaide et al. ................ 378/62 |
| 2012/0294421 A1* | 11/2012 | Mukaide et al. ................ 378/62 |

FOREIGN PATENT DOCUMENTS

| | | |
|---|---|---|
| JP | 2010502977 A | 1/2010 |
| WO | 2008029107 A2 | 3/2008 |
| WO | WO 2008029107 A2 * | 3/2008 |
| WO | 2009115966 A1 | 9/2009 |

* cited by examiner

X-RAY IMAGING APPARATUS AND X-RAY IMAGING METHOD

TECHNICAL FIELD

The present invention relates to an image pickup apparatus and an imaging method using X-rays.

BACKGROUND ART

A nondestructive testing using radiation is used in a wide range of fields from industrial use to medical use. For example, X-rays are electromagnetic waves having a wavelength in the range of approximately 1 pm to 10 nm ($10^{-12}$ to $10^{-8}$ m). Among such X-rays, those having shorter wavelengths are referred to as hard X-rays, and those having longer wavelengths are referred to as soft X-rays.

An absorption contrast method using the difference in transmittance of X-rays transmitted through a test object is put to practical use in security related fields, such as internal crack inspection performed on steel and baggage inspection, by applying the high penetrative power of X-rays in the absorption images acquired using the method.

For a test object that is constituted of materials having similar densities and having less contrast due to X-ray absorption, X-ray phase contrast imaging that detects a shift in the X-ray phase due to the test object is effective.

As one type of X-ray phase contrast imaging, an X-ray imaging apparatus that uses a splitting element divides an X-ray beam and that includes a mask to block the X-ray beam at the edges (borders of pixel) of the pixels in a detector is disclosed in PTL 1. In this apparatus, units are set such that an X-ray beam is incident on part of an X-ray shielding mask when the test object is not present. Then, when the test object is disposed, the X-ray beam is refracted at the test object, and the position of the X-ray beam incident on the X-ray shielding mask changes. Since the amount of X-ray blocked by the X-ray shielding mask changes in response to the amount of displacement of the X-ray beam, the refraction at the test object can be detected as a change in the X-ray intensity. As a result, it is possible to detect an X-ray phase shift due to the test object.

CITATION LIST

Patent Literature

PTL 1 International Publication No. 2008-029107

SUMMARY OF INVENTION

Technical Problem

With the X-ray imaging apparatus described in PTL 1, a mask that blocks X-rays is disposed in each pixel of the detector. However, when the transmittance of X-ray through objects is considered, heavy elements such as gold and platinum have to be used as the material of the masks, and thus production cost increases.

The masks used in the X-ray imaging apparatus described in PTL 1 have to have a high aspect ratio to ensure the light-shielding capability. However, such high-aspect-ratio masks are difficult to manufacture. X-ray diffusion at the mask wall may influence image quality. Accordingly, the present invention provides an X-ray imaging apparatus and an X-ray imaging method that does not use X-ray-shielding masks and detect refraction of an X-ray beam at a test object as a change in X-ray intensity.

Solution to Problem

The X-ray imaging apparatus according to the present invention includes a splitting element configured to spatially divide an X-ray emitted from an X-ray source; a scintillator configured to emit light when a divided X-ray beam divided at the splitting element is incident on the scintillator; a light-transmission limiting unit configured to limit transmitting amount of the light emitted from the scintillator; and a plurality of light detectors each configured to detect the amount of light that has transmitted through the light-transmission limiting unit, wherein the light-transmission limiting unit is configured such that a light intensity detected at each of the light detectors changes in response to a change in an incident position of the X-ray beam. The method of X-ray imaging according to the present invention includes the steps of spatially dividing an X-ray emitted from an X-ray source; emitting light when the spatially divided X-ray beam is incident on the scintillator; and acquiring information about a phase shift of the X-ray beam due to a test object using a light-transmission limiting unit configured such that a light intensity detected at each of the light detectors changes in response to a change in an incident position of the X-ray beam.

Advantageous Effects of Invention

The present invention provides an X-ray imaging apparatus and an X-ray imaging method that does not use X-ray-shielding masks and detect refraction of an X-ray beam at a test object as a change in X-ray intensity.

DESCRIPTION OF EMBODIMENTS

Figure 1:
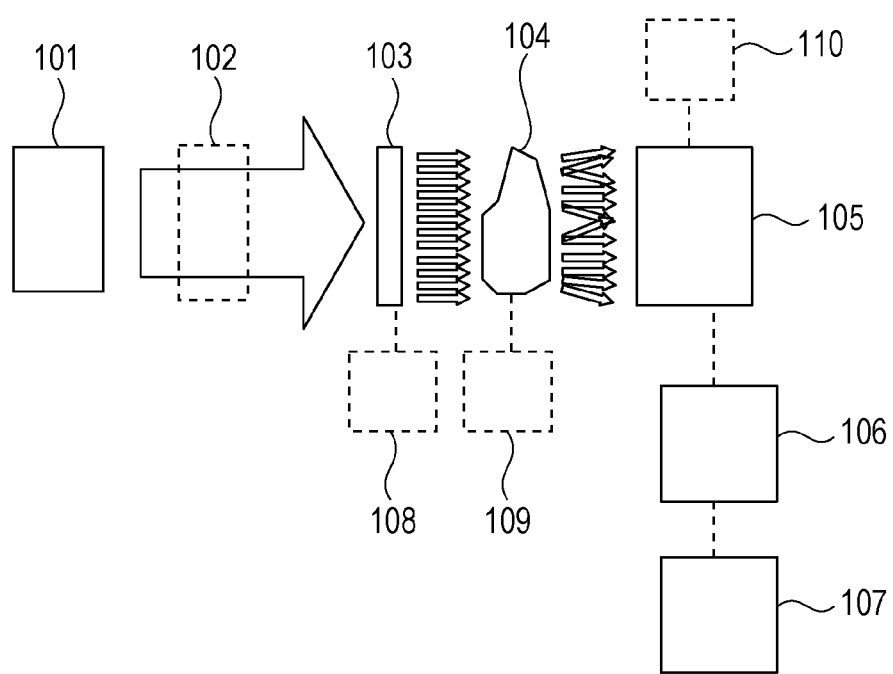
FIG. 1 is a schematic view of an X-ray imaging apparatus according to first, second, third, fourth, fifth, and sixth embodiments of the present invention.

An X-ray imaging apparatus according to embodiments of the present invention is configured to acquire X-ray phase shift information based on the amount of X-ray displacement or a change in X-ray intensity distribution that occur when an X-ray beam is transmitted through a test object.

The configuration of such X-ray imaging apparatus is set such that, when phase shift in an X-ray beam due to a test object is used, the detection range of X-ray beam movement and the change in the X-ray intensity distribution are sufficient.

Specifically, a light-transmission limiting unit that limits the amount of transmitting light, emitted from a scintillator is used to detect a minute X-ray displacement or a minute change in X-ray intensity distribution due to the refraction of an X-ray beam at a test object. The light-transmission limiting unit is, for example, a light-shielding unit that has light-shielding masks to block part of the light emitted from the scintillator or a light-attenuating unit that has optical filters to attenuate the light. Such light-shielding unit and light-attenuating unit are capable of changing the amount of light transmitted through an area corresponding to a single pixel on the basis of a displacement of an incident X-ray or a change in the X-ray intensity distribution. Thus, by detecting the amount of light that has passed through the light-shielding unit or the light-attenuating unit, information associated with a displacement of the incident X-ray beam and a change in the intensity distribution can be acquired.

As described in a third embodiment, a light-shielding unit having two different types of light-shielding masks, which detect different amounts of light intensity changes per unit length in the X-ray movement direction, may be used to acquire differential phase contrast images and so on that take into consideration X-ray absorption information (transmittance) of the test object.

For example, a first light-shielding mask that transmits a greater amount of light when the X-ray incident position is moved in a predetermined direction and a second light-shielding mask that transmits a smaller amount of light may be used. In such a case, it is desirable that the first area containing the first light-shielding mask and the second area containing the second light-shielding mask adjoin each other.

As described in a fourth embodiment, a light-shielding unit including a first area containing a light-shielding mask and a second area not containing a light-shielding mask may be used to acquire differential phase contrast images and so on that take into consideration X-ray absorption information (transmittance) of the test object. In such a case, it is desirable that the first and the second area adjoin each other.

As described in a fifth embodiment, first detecting pixels that are shielded from part of the incident light and second detecting pixels that are not shielded from the incident light may be used to acquire differential phase contrast images and so on that take into consideration X-ray absorption information (transmittance) of the test object.

As described in a sixth embodiment a light-attenuating unit including an area containing two different types of optical filters that provide different changes in the detected light intensity per unit displacement in the movement direction of the X-ray beam may be used to acquire differential phase contrast images and so on that take into consideration X-ray absorption information (transmittance) of the test object.

For example, a first optical filter configured such that light transmittance increases when the X-ray incident position moves in a predetermined direction and a second optical filter configured such that the light transmittance decreases. In such a case, it is desirable that the first area containing the first optical filter and the second area containing the second optical filter adjoin each other.

As described in a seventh embodiment, a light-attenuating unit including a first area containing an optical filter and a second area not containing an optical filter may be used to acquire differential phase contrast images and so on that take into consideration X-ray absorption information (transmittance) of the test object. In this case, it is desirable that the first area and the second area adjoin each other.

Embodiments will be described in detail below with reference to the drawings.

First Embodiment

X-Ray Imaging Apparatus and Imaging Method Using Light-Attenuating Unit

An X-ray imaging apparatus that acquires images associated with a phase shift in a test object, e.g., differential phase contrast image and phase contrast image, will be described with reference to FIG. 1.

As illustrated in FIG. 1, the X-ray imaging apparatus according to this embodiment includes a splitting element 103 disposed on an optical path of an X-ray beam emitted from an X-ray source 101, a test object 104, and a detecting unit 105. In addition, transporting units 108, 109, and 110, such as stepping motors, that move the splitting element 103, the test object 104, and the detecting unit 105 may be provided. For example, since the test object 104 can be appropriately moved using the transporting unit 109, an image of a specific section of the test object 104 can be acquired.

An X-ray generated at the X-ray source 101 is spatially divided at the splitting element 103. Specifically, the splitting element 103 functions as a sample mask having a plurality of apertures, which is described in PTL 1, and the X-ray transmitted through the splitting element 103 form fluxes of X-ray. The splitting element 103 is, for example, a slit array having lines and spaces. Instead, the splitting element 103 may be a pinhole array. The regions through which the X-ray beams are transmitted may be arranged one-dimensionally or two-dimensionally.

The slits in the splitting element 103 may not penetrate the substrate of the splitting element so long as X-rays transmit through. The material of the splitting element 103 may be selected from materials having a high X-ray absorbance, such as Pt, Au, Pb, Ta, or W. The material may instead be compounds containing these materials.

The interval of the line-and-space pattern of the X-rays divided by the splitting element 103 and incident on the position of the detecting unit 105 is greater than the pixel size of the detecting unit 105. Specifically, the size of the pixels included in the detecting unit 105 is smaller than the spatial interval of the X-rays divided at the splitting element 103 and projected on the detecting unit 105.

The phase of an X-ray beam obtained through spatial division at the splitting element 103 shifts by the test object 104, and the X-ray beam is refracted. The refracted X-ray beam is detected by the detecting unit 105. Signal processing is performed by a computing unit 106 on the information related to the X-ray beam acquired by the detecting unit 105. Then, the processed information is output to a display unit 107, such as a monitor.

The test object 104 may be an animal, a plant, a person, an organic material, an inorganic material, or an organic/inorganic composite.

When a monochromatic X-ray is used, a monochromatizing unit 102, such as a monochrometer or an X-ray multilayer mirror, combined with slits may be disposed between the X-ray source 101 and the splitting element 103.

A grid, which is used for X-ray imaging, may be disposed between the test object 104 and the detecting unit 105 to reduce the ambiguity of an image formed by X-ray beams scattered by the test object 104.

Figure 2:
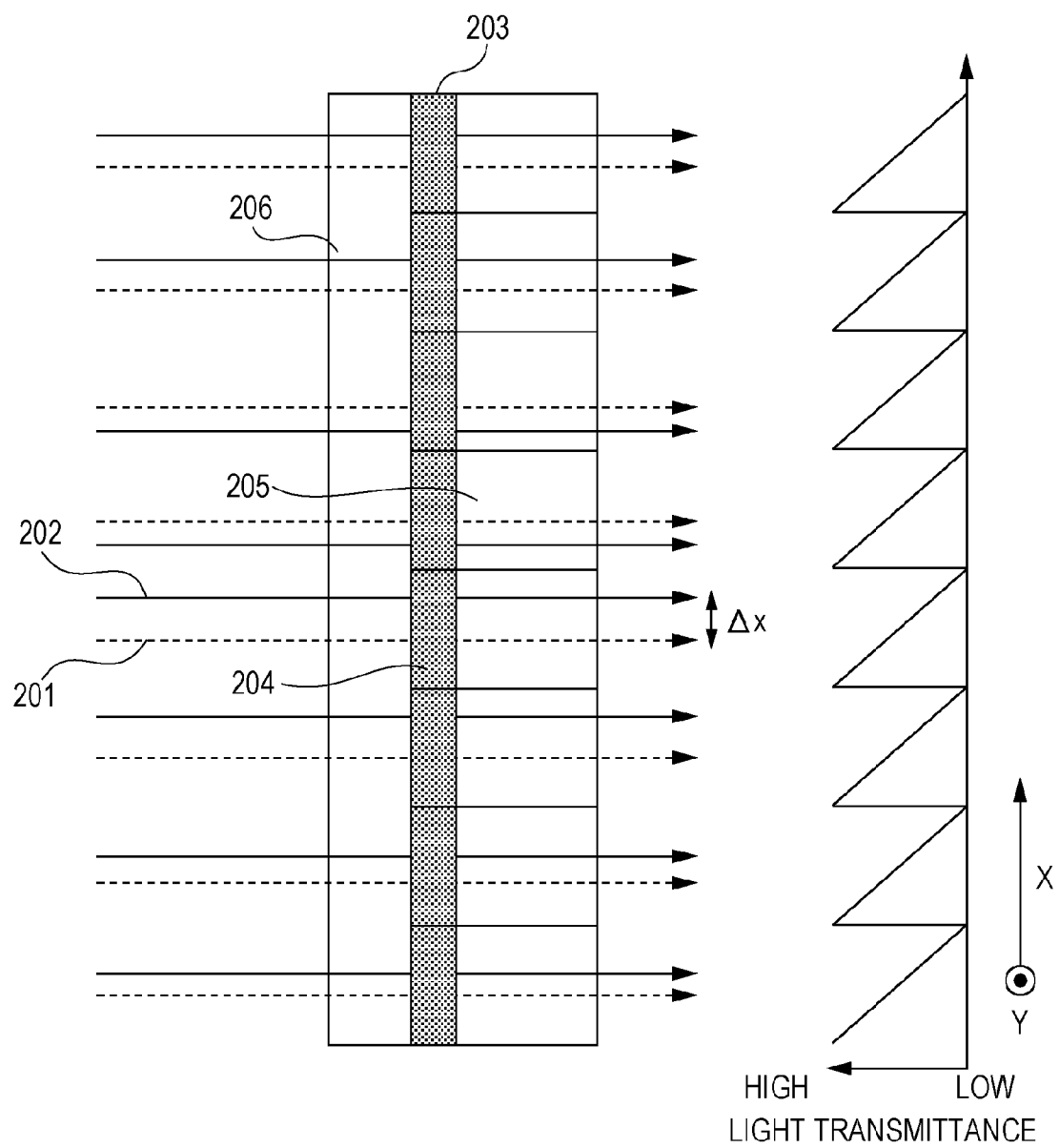
FIG. 2 is a schematic view of a detecting unit according to the first embodiment of the present invention.

With reference to FIG. 2, the detecting unit 105 according to this embodiment will be described. The detecting unit 105 includes a scintillator 206, a light-attenuating unit 203, and light detectors 205. Since the light detectors 205 are arranged two-dimensionally, each light detector 205 is equivalent to a pixel of a detected image.

The scintillator 206 is sensitive to X-rays and converts an X-ray beam to light detectable by the light detectors 205. For example, cesium iodide (CsI) is used as the scintillator 206. The light detectors 205 have sensitivity in the light-emitting wavelength range of the scintillator and are, for example, photoelectric conversion elements including a semiconductor, such as single crystal silicon or poly crystal silicon. The scintillator 206, the light-attenuating unit 203, and the light detectors 205 may be integrated into a unit, as illustrated in FIG. 2, or may be disposed separately from each other.

In FIG. 2, a reference X-ray beam 201 is a divided X-ray beam when the test object 104 is not disposed, and an X-ray beam 202 is an X-ray beam refracted by the test object 104. It is desirables to set the units such that the reference X-ray beam 201 is transmitted through the center of a light detector 205.

The light-attenuating unit 203 includes a plurality of optical filters 204. The light transmittance of the each optical filter 204 change gradually in a continuous or step-wise manner in the X direction (a direction orthogonal to the incident X-ray beam). The optical filter 204 is constituted of metal plates having continuously different thicknesses stacked on a light-transmissive substrate. Hereinafter, the term "continuously" includes the concept of "step-like."

With such a configuration, when the X-ray beam 202 is displaced in the X direction with respect to the reference X-ray beam 201, the signal intensity detected at the light detectors 205 changes. Thus, the displacement from the reference X-ray beam 201 due to the test object 104 can be acquired from the detected intensity.

For example, when $I_0$ represents the intensity of the reference X-ray beam 201 detected by the light detector 205 and I represents the intensity of the X-ray beam 202, which corresponds to the displacement $\Delta x$ from the reference X-ray beam 201, and when the relationship between these intensities is, for example, linear, the intensity I detected by the light detector 205 is defined by Expression 1.

$$I = I_0 + a\Delta x \quad (1),$$

where a represents a constant. By using this expression, the displacement of an X-ray beam can be acquired from the detected intensity I. Here, X-ray absorption by the test object 104 is not considered.

Figure 3:
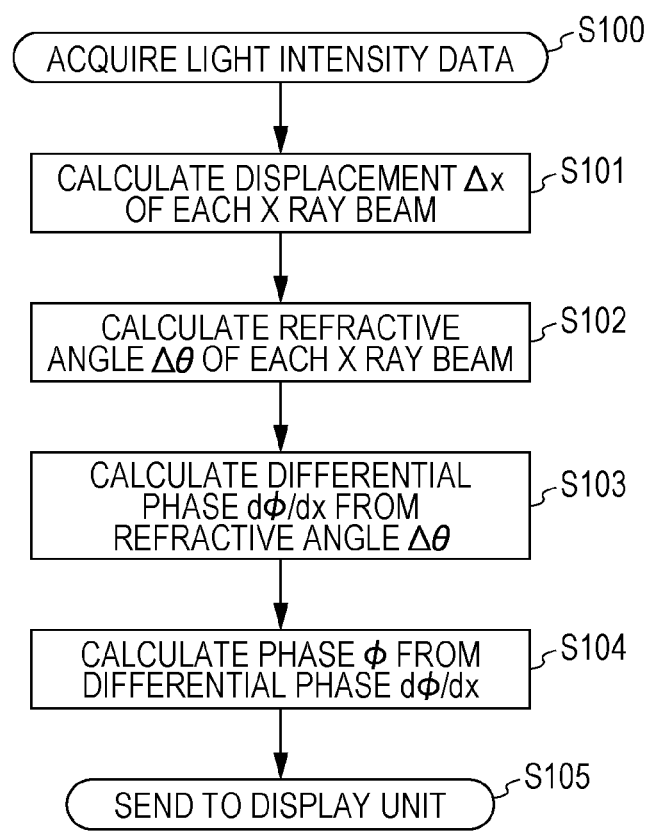
FIG. 3 is flow chart illustrating the process performed by a computing unit according to the first and second embodiments of the present invention.

The computation process is illustrated in FIG. 3. First, light intensity information for each X-ray beam is acquired (S100). Next, the displacement $\Delta x$ from the reference X-ray beam 201 is calculated from the light intensity I detected at each light detector 205 (S101). The displacement $\Delta x$ may instead be determined by referring, on the basis of the measured intensity, to a data table, which is stored in the computing unit 106 or another memory and contains the correspondence relationship between the detected intensity of light when the test object 104 is not disposed and the position x of the X-ray beam.

Next, the refractive angle $\Delta\theta$ of each X-ray beam is calculated using Expression 2 (S102).

$$\Delta\theta = \tan^{-1}\left(\frac{\Delta x}{Z}\right) \quad (2)$$

Here, $\Delta x$ represents the displacement from the reference X-ray beam 201, and z represents the distance from the test object 104 to the detecting unit 105.

Using Expression 3, a differential phase $d\phi/dx$ of a light detector (pixel) 205 is calculated to acquire differential phase information (S103).

$$\frac{d\phi}{dx} = \frac{2\pi}{\lambda}\Delta\theta \quad (3)$$

Here, $\lambda$ represents the wavelength of an X-ray beam and, when continuous X-ray is used, represents the effective wavelength.

Next, a phase $\phi$ is calculated by integrating the acquired differential phases $d\phi/dx$ in the x direction to acquire phase information (S104). The display unit 107 can display images such as an image of the displacement $\Delta x$ calculated in this way, a differential phase contrast image $d\phi/dx$, and an X-ray phase contrast image $\phi$, as well as a measured intensity distribution image (S105).

With the above-described configuration, production costs are not increased since X-ray shielding masks using heavy elements that block X-ray are not required. Furthermore, X-ray shielding masks having a high aspect ratio, which is difficult to manufacture, is not required. Furthermore, the influence of scattering at the X-ray shielding masks can be reduced, and thus, high-quality images can be formed.

With reference to FIG. 2, an optical filter having a transmittance gradient in the X direction indicated on the page has been described. Instead, an optical filter having a transmittance gradient in the direction perpendicular to the face of page (Y direction) may be used.

By using a two-dimensional pinhole array as the splitting element 103 and using optical filters having transmittance gradients in the X and Y directions, it is possible to detect a phase gradient two-dimensionally.

A phase gradient may be two-dimensionally detected by stacking optical filters having a transmittance gradient in the X direction and optical filters having a transmittance gradient in the Y direction.

Second Embodiment

X-Ray Imaging Apparatus and Imaging Method Using Light-Shielding Unit

Figure 4:
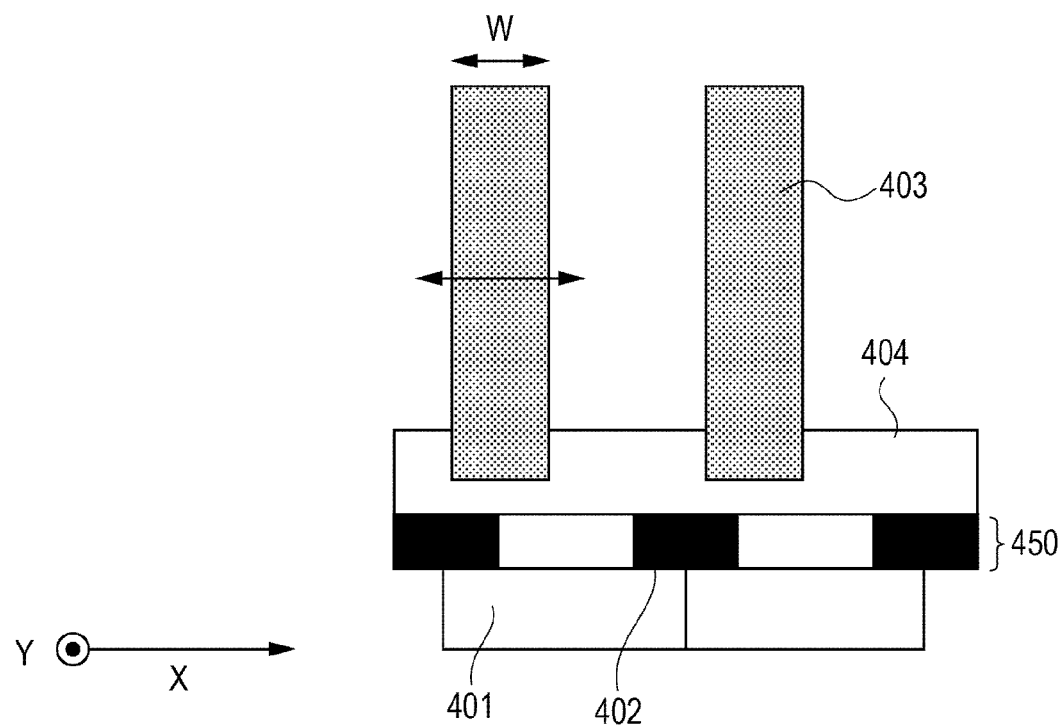
FIG. 4 is a schematic view of a detecting unit according to the second embodiment of the present invention.

In a second embodiment, an X-ray imaging apparatus and an imaging method using a light-shielding unit instead of the light-attenuating unit 203 of the first embodiment will be described. Specifically, in this embodiment, a detecting unit 105 different from the detecting unit 105 described in the first embodiment will be used. The configuration of other units is the same as that of the first embodiment. FIG. 4 illustrates part of the detecting unit 105 and is a view in a direction orthogonal to the X-ray incident direction. Specifically, with reference to FIG. 4, an X-ray beam 403 enters from the top to the bottom and the position of the X-ray beam changes in the transverse direction due to refraction.

With reference to FIG. 4, a light-shielding mask 402 is disposed above the edge of a light detector 401 (i.e., border of light detectors). The light-shielding mask 402 blocks part of the light emitted from a scintillator 404. A light-shielding unit 405 includes an array of light-shielding masks 402.

The light-shielding mask 402 blocks light in the wavelength range of light emitted from the scintillator 404 and is, for example, constituted of a plastic film on which a black light-shielding pattern is printed or on which a metal light-shielding pattern is deposited.

It is desirable to set the units such that the X-ray beam 403 is incident on the scintillator 404 such that the center of the X-ray beam 403 in the X direction aligns with the edge of the light-shielding mask 402 in the X direction. Here, w represents the width of the X-ray beam 403.

With such an arrangement, when an X-ray beam is incident on the test object 104, the position of the incident X-ray beam 403 on the scintillator 404 changes due to refraction. Since the detected intensity of the light emitted from the scintillator 404 changes due to this displacement, the displacement can be detected as a change in the light intensity.

The light intensity I detected by the light detector 401 when the X-ray beam 403 is refracted at the test object 104 and displaced by $\Delta x$ in the X direction can be represented by, for example Expression 4.

$$I = \left(1 + \frac{2\Delta x}{W}\right) I_0 \quad (4)$$

$I_0$ represents the light intensity detected when the test object 104 is not disposed. Since the scintillator 404 is sufficiently thin, Expression 4 does not take into consideration diffusion of light inside the scintillator 404.

Accordingly, the displacement $\Delta x$ can be determined from the light intensity $I_0$ detected when the test object 104 is not disposed and the light intensity I detected when the test object 104 is disposed. In consideration of diffusion of light inside the scintillator 404, the displacement $\Delta x$ of the X-ray beam may be determined by referring, on the basis of the measured intensity, to a data table, which is stored in the computing unit 106 and contains the correspondence relationship between the light intensity detected when the test object 104 is not disposed and the position x of the X-ray beam.

Similar to the first embodiment, through the computation process, an image of displacement $\Delta x$, a differential phase contrast image $d\phi/dx$, and an X-ray phase contrast image $\phi$, and so on can be acquired.

With reference to FIG. 4, a configuration having sensitivity only in X-direction displacement has been described above. Instead, a light-shielding mask having sensitivity in displacement in the direction perpendicular to the face of the page (Y direction) may be used.

By using a pinhole array as the splitting element 103 and using a light-shielding mask having sensitivity to displacement in the X and Y directions, it is possible to detect a phase gradient in a two-dimensional direction.

A phase gradient in a two-dimensional direction may be detected by stacking a light-shielding mask having sensitivity to displacement in the X direction and a light-shielding mask having sensitivity to displacement in the Y direction.

Third Embodiment

Light-Shielding Unit that Calculates Transmittance

In a third embodiment, an X-ray imaging apparatus and an imaging method suitable when a test object has sufficient X-ray absorbance will be described.

Figure 5:
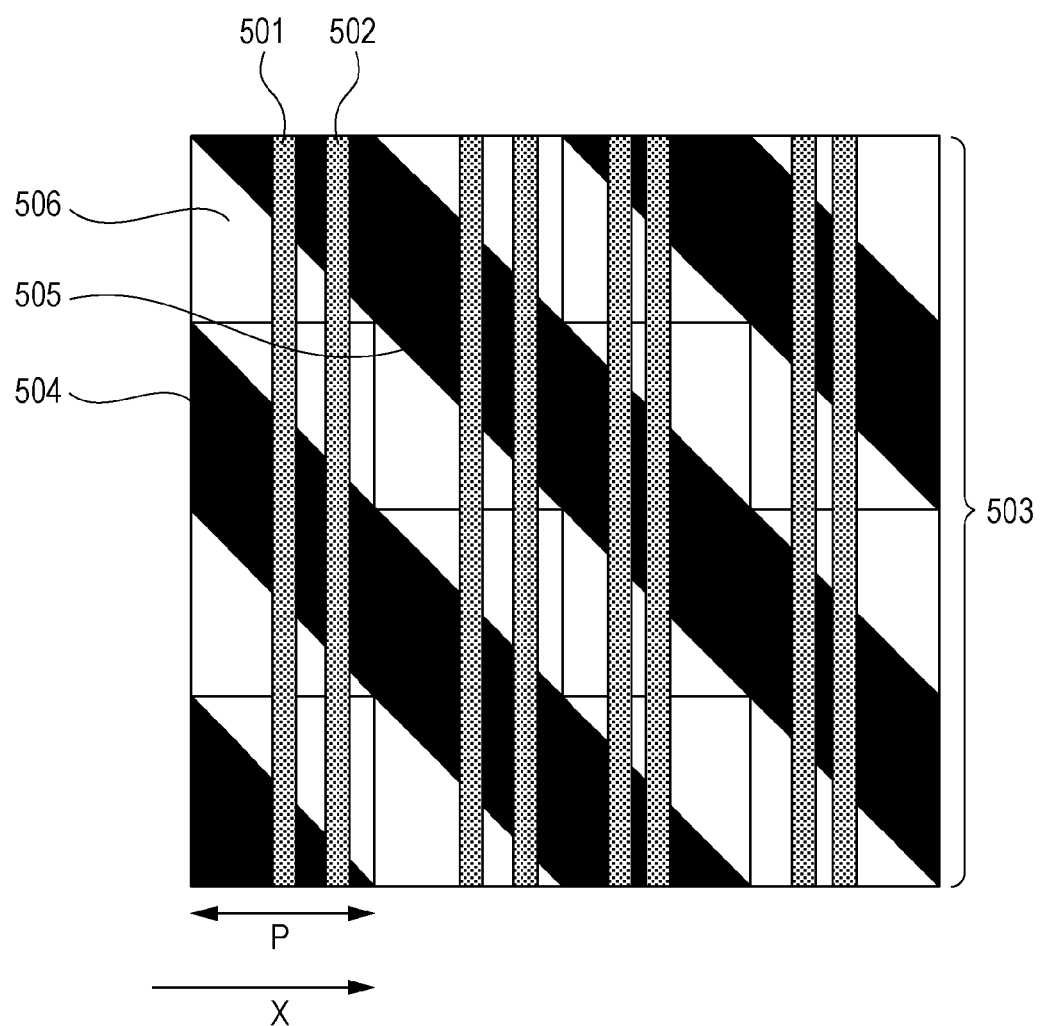
FIG. 5 is a schematic view of a light-shielding unit according to the third embodiment of the present invention.

In this embodiment, a light-shielding unit 503, which is illustrated in FIG. 5, is used instead of the light-shielding unit 405 of the second embodiment. The configuration of other units is the same as that of the first embodiment.

With reference to FIG. 5, the light-shielding unit 503 according to this embodiment will be described. FIG. 5, which illustrates the light-shielding unit 503, is a schematic view of part of the detecting unit 105 illustrated in FIG. 1. In other words, the detecting unit 105 has a layered structure in which a scintillator, the light-shielding unit 503, and light detectors are disposed in order from the X-ray incident direction.

A reference X-ray beam 501 defines a divided X-ray beam when the test object 104 is not disposed, and an X-ray beam 502 defines an X-ray beam refracted by the test object 104. It is desirable to set the units such that the reference X-ray beam 501 is incident on the center of a pixel 506 in the X direction. The light-shielding unit 503 is constituted of alternately disposed light-shielding masks 504 (first light-shielding mask), which are structures in which the intensity of light detected by light detectors becomes greater for movement in the X direction, and light-shielding masks 505 (second light-shielding mask), which are structures in which the intensity of light detected by a light detector becomes smaller for movement in the X direction. Specifically, the light-shielding unit 503 is a structure having two different types of light-shielding masks 504 and 505, which each detect a different amount of change in the light intensity per unit length when an X-ray beams moves in the X direction.

The X-ray beam from the test object 104 incident on the detecting unit 105 after moving by $\Delta x$ enters a scintillator inside a detecting unit, and the light intensity $I'_1$ of light emitted from the scintillator and transmitted through the light-shielding mask 504 is represented by, for example, Expression 5.

$$I'_1 = A I_{01}\left(\frac{1}{2} + \frac{\Delta x}{P}\right) \quad (5)$$

$I_{01}$ represents the light intensity of light emitted from the scintillator in response to the X-ray beam incident on the scintillator, which is equivalent to a pixel 506, when the test object 104 is not disposed, and P represent the length of a side of the pixel 506. A represents the X-ray transmittance of the test object 104.

The X-ray beam from the test object 104 incident on the detecting unit 105 after moving by $\Delta x$ is incident on the scintillator inside the detecting unit, and, in response, light is emitted. The light intensity $I'_2$ of light emitted from the scintillator via the light-shielding mask 505 is represented by Expression 6.

$$I'_2 = A I_{02}\left(\frac{1}{2} - \frac{\Delta x}{P}\right) \quad (6)$$

$I_{02}$ represents the light intensity of light emitted from the scintillator in response to the X-ray beam incident on the scintillator, which is equivalent to a pixel 506, when the test object 104 is not disposed. When $I_1$ and $I_2$ represent the light intensities of the reference X-ray beam 501 detected at the light-shielding masks 504 and 505, respectively, the displacement $\Delta x$ can be derived from Expressions 5 and 6 and represented by Expression 7.

$$\Delta x = \frac{P(I'_1 I_2 - I_1 I'_2)}{2(I'_1 I_2 + I_1 I'_2)} \quad (7)$$

In this way, since $\Delta x$ can be determined by Expression 7, transmittance A of the test object 104 can also be determined by using $\Delta x$.

Even when two different types of light-shielding masks do not form a symmetrical structure, the displacement $\Delta x$ and the transmittance A may be determined by referring to a data table, which is stored in the computing unit 106 and contains the correspondence relationship between the light intensity detected when the test object 104 is not disposed and the position x in the pixel 506.

Specifically, by formulating the light intensity detected at a position x on the basis of the above-described data table associated with two different types of light-shielding masks, the displacement $\Delta x$ and the transmittance A can be determined.

The transmittance based on absorption of the test object 104 and the displacement due to refraction can be determined from the relationship between the light intensity of the reference X-ray beam 501 and the light intensity of the X-ray beam 502 detected at adjoining light-shielding masks 504 and 505, respectively. The light-shielding masks 504 and 505 are disposed obliquely intersecting the X-rays. However, the light-shielding masks 504 and 505 may be disposed in any pattern so long as the displacement of X-rays can be acquired.

In this case, since information about X-ray intensity at two regions, i.e., the light-shielding mask 504 and the light-shielding mask 505, is used, the spatial resolution in the x direction is reduced to one-half. Thus, in addition to the above-described measurements, it is possible to perform similar measurements after moving the splitting element 103 and the detecting unit 105 or the test object 104 in the X direction by a length equal to the length of the light-shielding mask 504 in the X direction.

In this way, information about the X-ray transmittance A and the displacement $\Delta x$ corresponding to the position of the test object 104 of which the X-ray displacement has already been measured can be acquired.

By detecting the light intensity by the detecting unit 105, the transmittance A, the differential phase $d\phi/dx$, and the phase $\phi$ can be calculated using the computing unit 106. An X-ray transmittance image, a displacement image $\Delta x$, a differential phase contrast image $d\phi/dx$, and an X-ray phase contrast image $\phi$ can be displayed on the display unit 107.

Figure 6:
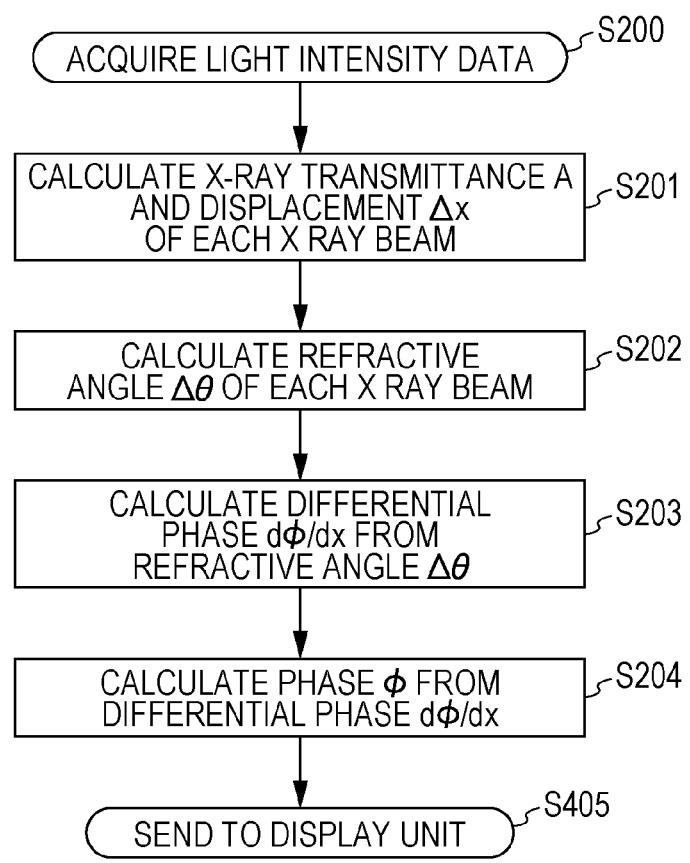
FIG. 6 is flow chart illustrating the process performed by a computing unit according to the third, fourth, fifth, and sixth embodiments of the present invention.

The computation process will be described with reference to FIG. 6. First, intensity information of each X-ray beam is acquired (S200). Next, the displacement $\Delta x$ from the reference X-ray beam 501 and X-ray transmittance A is calculated from the detected light intensity of each X-ray beam 502 (S201).

Next, the refractive angle $\Delta\theta$ of each X-ray beam is determined in such a manner similar to the first embodiment by using the displacement $\Delta x$ and the distance Z between the test object 104 and the detecting unit 105 (S202).

The differential phase $d\phi/dx$ is calculated from the refractive angle $\Delta\theta$ of each X-ray beam (S203). Next, the phase $\phi$ is calculated by integrating the acquired differential phases $d\phi/dx$ in the X direction (S204).

Images calculated in this way, such as an X-ray transmittance image, a displacement image, a differential phase contrast image, and a phase contrast image, can be displayed on the display unit 107 (S205). The measured-intensity distribution image can also be displayed in a similar manner. According to such a configuration, differential phase contrast images and phase contrast images that take absorption into consideration can be acquired.

Fourth Embodiment

Another Light-Shielding Unit that Calculates Transmittance

In the fourth embodiment, an X-ray imaging apparatus and an imaging method suitable when a test object has sufficient X-ray absorbance will be described.

Figure 7:
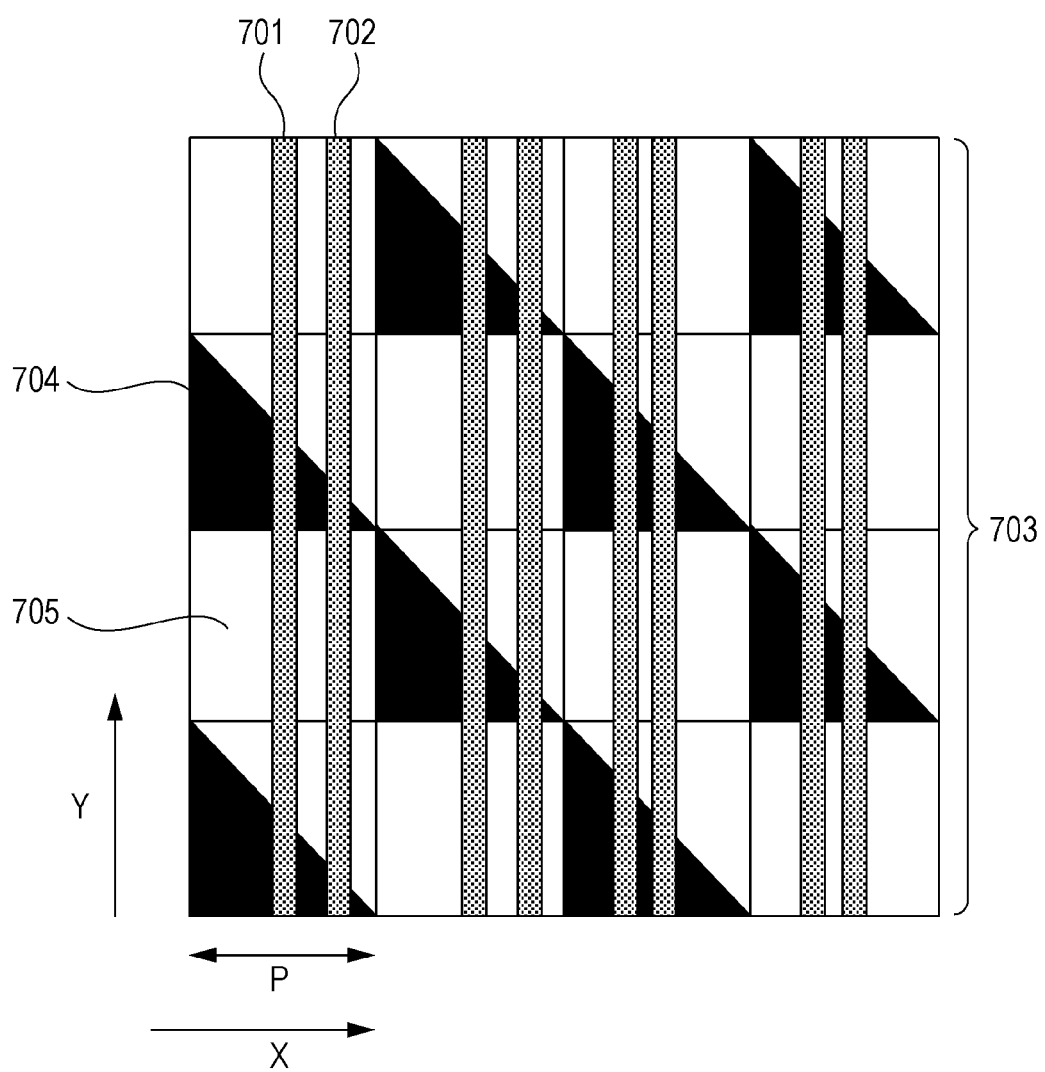
FIG. 7 is a schematic view of a light-shielding unit according to the fourth embodiments of the present invention.

In this embodiment, a light-shielding unit 703, which is illustrated in FIG. 7, is included instead of the light-shielding unit 405 of the second embodiment. Specifically, in this embodiment, an area containing a part that blocks light emitted from a scintillator and an area not containing a part that blocks light are provided. The other basic configuration of the apparatus is the same as that of the first embodiment.

FIG. 7, which illustrates the light-shielding unit 703, is a schematic view of part of the detecting unit 105 illustrated in FIG. 1. In other words, the detecting unit 105 has a layered structure in which a scintillator, the light-shielding unit 703, and light detectors are disposed in order from the X-ray incident direction. A linear X-ray beam spatially divided by the splitting element 103 is incident on the test object 104, and the transmitted X-ray beam is incident on the detecting unit 105.

A reference X-ray beam 701 defines a divided X-ray beam when the test object 104 is not disposed, and an X-ray beam 702 defines an X-ray beam refracted by the test object 104. It is desirable to set the units such that the reference X-ray beam 701 is incident on the center of a light-shielding mask 704 in the X direction.

The light-shielding unit 703 is constituted of alternately arranged areas having light-shielding masks 704 and areas 705 in which the detected intensity of light emitted from the scintillator is unchanged when moved in the X direction. Here, the detected intensity of light emitted from the scintillator is unchanged when moved in the X direction is equivalent to the detected intensity of light being substantially unchanged. In other words, so long as absorption information can be acquired, the light intensity may change slightly when moved in the X direction.

With such a configuration, the X-ray transmittance A of the test object 104 can be determined from the area 705 not containing the light-shielding mask 704. As a result, the transmittance of an area containing the light-shielding mask 704 can be determined in a complementary manner from the transmittance A of the area 705 not containing the light-shielding mask 704.

Similarly, since the refractive angle of the X-ray beam 702 in the area containing the light-shielding mask 704 can be determined, similar to the transmittance A, the refractive angle in the area 705 not containing the light-shielding mask 704 can be determined in a complementary manner.

The light-shielding masks 704 are disposed obliquely intersecting the X-ray beams. However, the light-shielding masks 704 may be disposed in any pattern so long as the displacement of X-ray beams can be determined.

In this case, since information about X-ray intensity in two different areas, i.e., the light-shielding masks 704 and the areas 705 not containing the light-shielding masks 704, is used, the spatial resolution in the X direction is reduced to one-half.

Thus, in addition to the above-described measurement, it is possible to perform a similar measurement by moving the splitting element 103 and the detecting unit 105 or the test object 104 in the X and Y direction and by moving the light-shielding unit 703 by a distance equal to a pixel. In this way, information about the X-ray transmittance A and the refractive angle corresponding to the position of the test object 104 of which X-ray displacement has already been measured can be acquired. The flow chart for the computing unit 106 is the same as that of the third embodiment. With the above-described configuration, differential phase contrast images and phase contrast images that take into consideration absorption can be acquired.

By using a pinhole array as the splitting element 103 and appropriately setting the shape of the light-shielding masks 704, it is possible to provide sensitivity not only for X-ray movement in the X direction but also in the Y direction. In such a case, it is desirable to set the units such that the reference X-ray beam 701 is incident on the center of the light-shielding mask 704 in the X and Y directions. In such a case, by dividing the X-ray intensity in an area of the light-shielding mask 704 by the transmittance A, an image associated with phase shift can be acquired. With the above-described configuration, images associated with X-ray phase shift taking into consideration absorption, e.g., differential phase contrast images and phase contrast images, can be acquired.

Fifth Embodiment

Another Light-Shielding Unit that Calculates Transmittance

Figure 8:
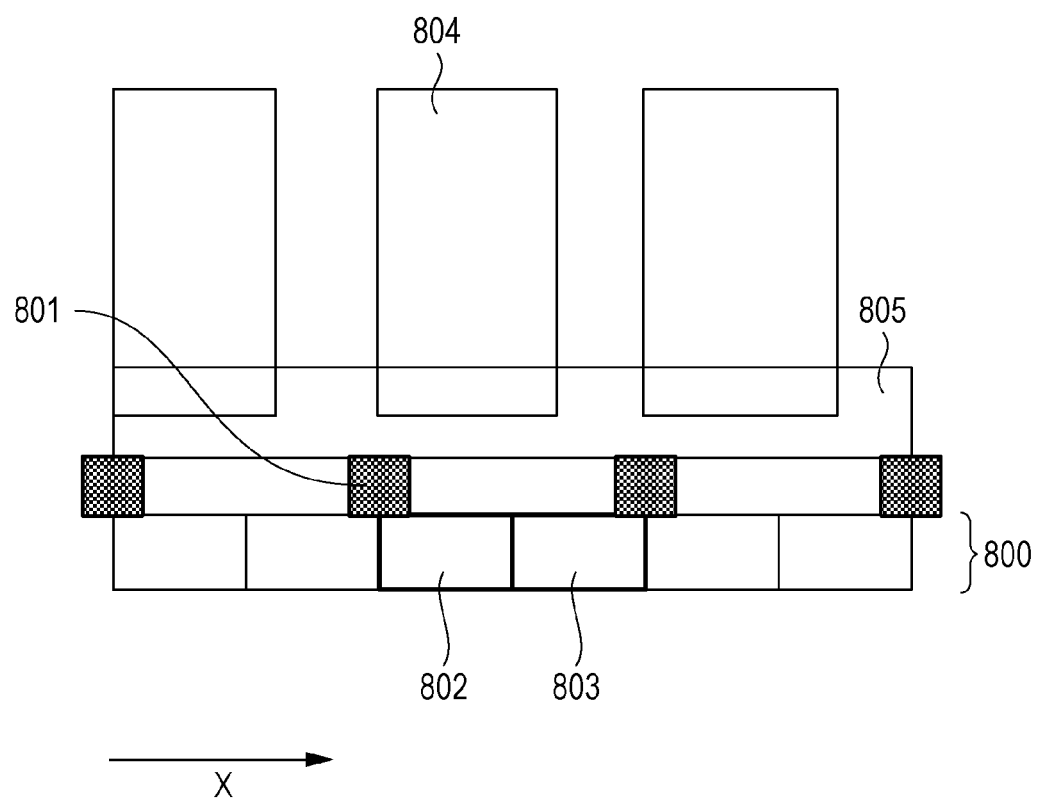
FIG. 8 is a schematic view of a detecting unit according to the fifth embodiment of the present invention.

In the fifth embodiment, an apparatus using a detecting unit, which is illustrated in FIG. 8, instead of the detecting unit of the first embodiment will be described. The apparatus configuration is the same as that of the first embodiment.

With reference to FIG. 8, a light detector 800 includes a plurality of pixel groups, each having a detecting pixel 802 and a detecting pixel 803. A light-shielding mask 801 is disposed at the border (edge) of the detecting pixel 802 and a detecting pixel adjoining to the left. A light-shielding mask is not provided at the edge of the detecting pixel 802 and the detecting pixel 803.

The arrangement interval L of the light-shielding mask 801 is L=2P, where P represents the size of the detecting pixel 802.

FIG. 8 illustrates an integrated unit of the light-shielding masks 801 and the light detector 800. Instead, the light-shielding mask 801 and the light detector 800 may be provided separately.

When an incident X-ray beam 804 is incident on a scintillator 805 with respect to the interval of the light-shielding masks 801, light is emitted from the scintillator 805. Part of this light is blocked at a light-shielding mask 801 in the X direction and enters both detecting pixels 802 and 803.

By such an arrangement, the light intensities detected at the detecting pixels 802 and 803 change due to absorption of the incident X-ray beam 804 by the test object 104. The light intensities detected at the detecting pixels 802 and 803 change due to displacement of an incident X-ray beam caused by refraction at the test object 104.

The intensity change due to absorption is the same in the detecting pixels 802 and 803. However, the intensity change with respect to displacement differs between the detecting pixels 802 and 803. For example, when an intensity change due to displacement occurs linearly, the displacements with respect to the intensity changes of the detecting pixels 802 and 803 are represented by Expressions 8 and 9.

$$\Delta X = a \frac{I_{802}}{A} + b \quad (8)$$

$$\Delta X = c \frac{I_{803}}{A} + d \quad (9)$$

$I_{802}$ and $I_{803}$ respectively represent the detected intensities at the detecting pixels 802 and 803, and A represents the X-ray transmittance of the test object 104. Specifically, by measuring $I_{802}$ and $I_{803}$ while moving the splitting element 103 when the test object 104 is not disposed, the measurement data can be fit into the expressions to acquire coefficients a, b, c, and d. (In this case, the X-ray transmittance A equals one.) Actually, when the test object 104 is measured, the X-ray transmittance A and the displacement $\Delta X$ can be acquired by solving simultaneous equations of the measured intensities and Expressions 8 and 9. The flow chart of the computing unit 106 is the same as that of the third embodiment. With the above-described configuration, displacement images, differential phase contrast images, and phase contrast images that take into consideration absorption can be acquired.

Sixth Embodiment

Light-Attenuating Unit that Calculates Transmittance

Figure 9:
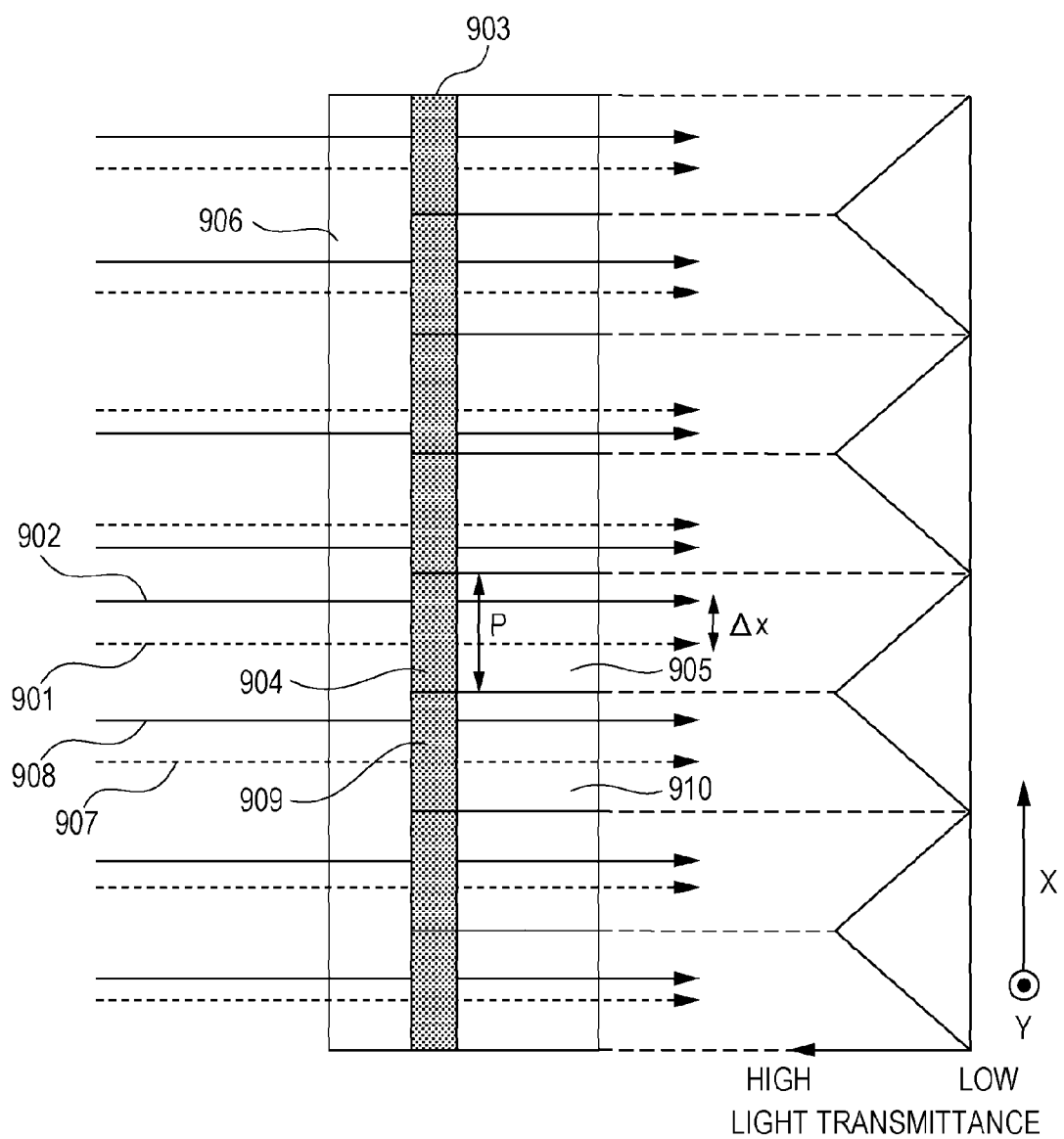
FIG. 9 is a schematic view of a detecting unit according to the sixth embodiment of the present invention.

In the sixth embodiment, an apparatus including a detecting unit, which is illustrated in FIG. 9, instead of the detecting unit of the first embodiment will be described. The apparatus configuration is the same as that of the first embodiment.

An X-ray beam spatially divided by the splitting element 103 illustrated in FIG. 1 is incident on the test object 104, and the transmitted X-ray beam is incident on the detecting unit 105. FIG. 9 is a schematic view of part of the detecting unit 105.

The detecting unit 105 includes a scintillator 906, a light-attenuating unit 903, and light detectors 905 and 910. Since the light detectors 905 and 910 are two-dimensionally arranged, each of the light detectors 905 and 910 is equivalent to a pixel in a detected image.

A reference X-ray beam 901 defines an X-ray beam divided when the test object 104 is not disposed and is incident on the scintillator 906 such that the X-ray beam is transmitted through the center of the light detector 905. An X-ray beam 902 defines an X-ray beam refracted at the test object 104. The light-attenuating unit 903 includes optical filters 904 (first optical filter) and optical filters 909 (second optical filter) arranged in a periodic manner.

The transmittance of the optical filters 904 (first optical filter) decreases as the light-emitting point of the scintillator 906 moves in the X direction. In other words, the movement of the light-emitting point causes a decrease in the intensity of detected light. In contrast, the transmittance of the optical filters 909 (second optical filter) increases as the light-emitting point of the scintillator 906 moves in the X direction. In other words, the movement of the light-emitting point causes an increase in the intensity of detected light. The light-attenuating unit 903 includes two different types of optical filters, which each detect a different amount of change in the light intensity per unit length when an X-ray beams moves in the X direction. With respect to FIG. 9, the light-attenuating unit 903 includes alternately-arranged optical filters 904 and 909 having symmetrical transmittance changes with respect to the X direction.

An optical filter represented by, for example, Expression 10 is used for the intensity of the light emitted from the scintillator 906 by the incident reference X-ray beam 901 detected by the light detector 905.

$$I_1 = I_0 e^{\alpha + \beta x_0} \quad (10)$$

$I_0$ represents the intensity of the light emitted when an X-ray beam spatially divided by the splitting element 103 is incident on the scintillator, $\alpha$ and $\beta$ represent constants, and $x_0$ represents the position of the reference X-ray beam 901 in the X direction. The intensity of the light emitted from the scintillator 906 by the incident X-ray beam 902 refracted at the test object 104 and detected by the light detector 905 is, for example, represented by Expression 11.

$$I_2 = I_0 A e^{\alpha + \beta x} \quad (11)$$

A represents the X-ray transmittance of the test object 104, and x represents the position of the X-ray beam 902 in the X direction. The displacement $\Delta x$ on the scintillator 906 can be determined from Expressions 8 and 9 using Expression 12.

$$\Delta x = \frac{1}{\beta} \ln\left(\frac{I_2}{I_1 A}\right) \quad (12)$$

Similar to the above, since the change in light transmittance of the optical filters 909 (second optical filter) in the X direction is symmetrical with that of the optical filters 904, the intensity $I'_1$ of the light emitted from the scintillator 906 by the incident reference X-ray beam 907 detected by the light detector 910 is represented by Expression 13.

$$I'_1 = I_0 e^{(\alpha + \beta P) - \beta x_0} \quad (13)$$

P represents the length of the optical filters 904 and 909 in the X direction. The intensity of light emitted from the scintillator 906 by the incident X-ray beam 908 refracted at the test object 104 detected by the light detector 910 is represented by Expression 14.

$$I'_2 = I_0 A e^{(\alpha + \beta P) - \beta x} \quad (14)$$

Based on Expressions 13 and 14, the displacement $\Delta x$ on the scintillator 906 can be represented by Expression 15.

$$\Delta x = \frac{1}{\beta} \ln\left(\frac{I'_1 A}{I'_2}\right) \quad (15)$$

Thus, based on Expressions 12 and 15, the X-ray transmittance A of the test object 104 can be determined using Expression 16.

$$A = \sqrt{\frac{I_2 I'_2}{I_1 I'_1}} \quad (16)$$

Specifically, the X-ray transmittance A is determined by the intensities $I_1$ and $I_2$ of the light emitted from the scintillator 906 by the incident reference X-ray beam 901 and the incident X-ray beam 902, respectively, transmitted through the optical filter and detected at the light detector 905 and the intensities $I'_1$ and $I'_2$ of the light emitted from the scintillator 906 by the incident reference X-ray beam 907 and the incident X-ray beam 908, respectively, and detected at the light detector 910. By substituting the X-ray transmittance A to Expression 12 or 15, the displacement $\Delta x$ can be determined.

With such a procedure, a highly precise differential phase contrast image or phase contrast image can be acquired for a test object that sufficiently absorbs X-rays since the X-ray transmittance of the test object 104 and the displacement can be calculated from two optical filters.

In such a case, since the differential phase contrast image is formed using information about the intensities detected in two regions, i.e., the optical filters 904 and 909, the spatial resolution is reduced to one-half.

To prevent such decrease in spatial resolution, it is also possible to perform a similar measurement by moving the splitting element 103 and the detecting unit 105 or the test object 104 in the X direction by a length equal to the optical filter 904 in the X direction. In this way, information about the X-ray transmittance A corresponding to the position of the test object 104 of which the X-ray displacement has been measured can be acquired.

The displacement $\Delta x$ and the X-ray transmittance A may be determined by referring to a data table, which is stored in the computing unit 106 and contains the correspondence relationship between the intensity of light detected when the test object 104 is not disposed and the position x inside the light detector 905. The flow chart of the computing unit 106 is the same as that of the third embodiment. With the above-described configuration, differential phase contrast images and phase contrast images that take into consideration absorption can be acquired.

Seventh Embodiment

Light-Attenuating Unit that Calculates Transmittance

Figure 10:
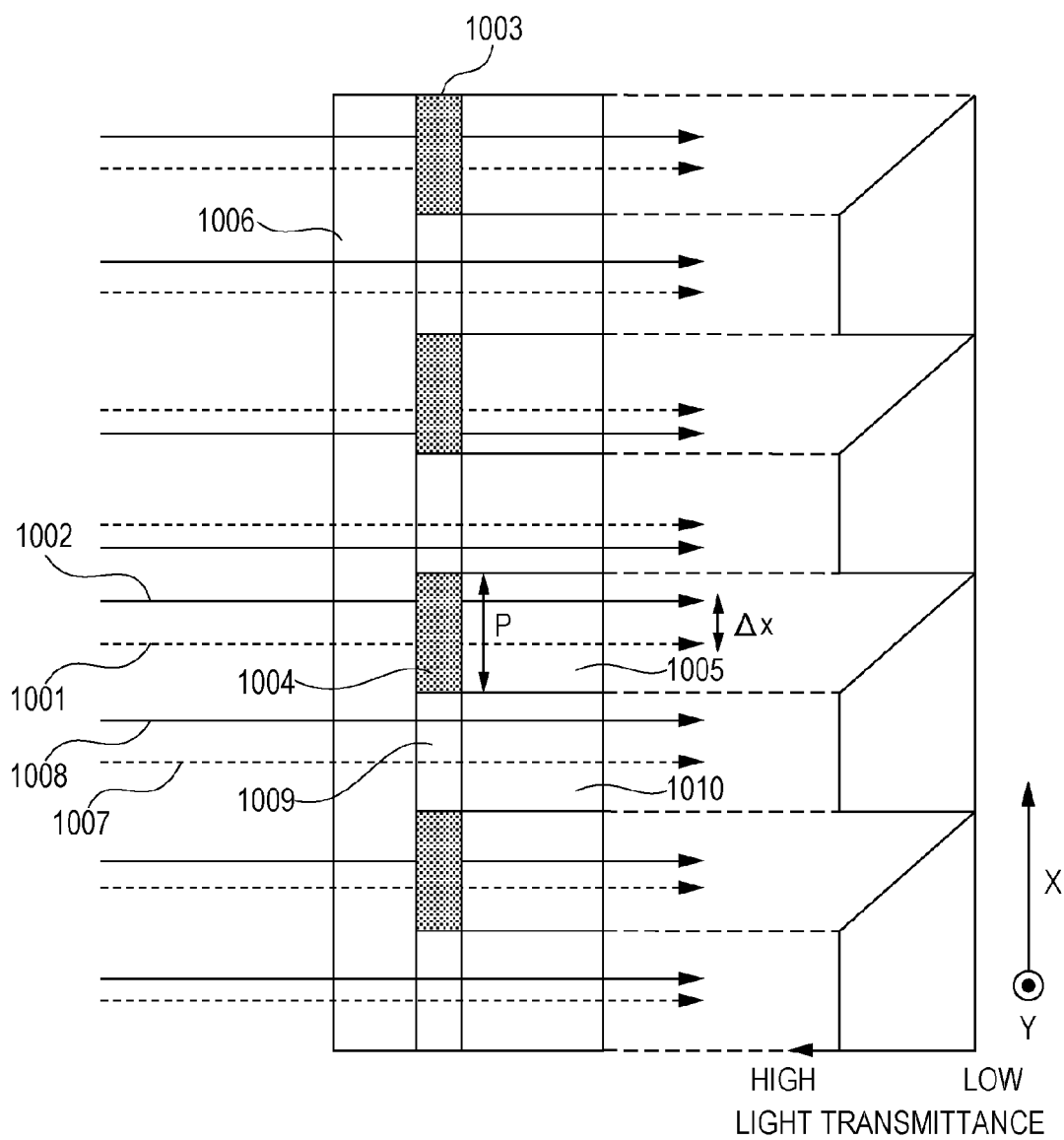
FIG. 10 is a schematic view of an X-ray imaging apparatus according to a seventh embodiment of the present invention.

In a seventh embodiment, an apparatus including a detecting unit, which is illustrated in FIG. 10, instead of the detecting unit 105 of the first embodiment will be described. The apparatus configuration is the same as that of the first embodiment. An X-ray beam spatially divided by the splitting element 103 is incident on the test object 104 and the transmitted X-ray beam is incident on the detecting unit 105. FIG. 10 is a schematic view of part of the detecting unit 105.

The detecting unit 105 includes a scintillator 1006, a light-attenuating unit 1003, and light detectors 1005 and 1010. Since the light detectors 1005 and 1010 are two-dimensionally arranged, each of the light detectors 1005 and 1010 is equivalent to a pixel in a detected image. A reference X-ray beam 1001 defines an X-ray beam divided when the test object 104 is not disposed and is incident on the scintillator 1006 such that the X-ray beam is transmitted through the center of the light detector 1005. An X-ray beam 1002 defines an X-ray beam refracted at the test object 104. The light-attenuating unit 1003 includes optical filters 1004 (first optical filter) and optical filters 1009 (second optical filter) arranged in a periodic manner.

The light intensity of the optical filters 1009 illustrated in FIG. 10 detected by the light detector 1010 is substantially unchanged with respect to the movement of an X-ray beam in the X direction.

An optical filter represented by Expression 10 is used for the intensity of the light emitted from the scintillator 1006 by the incident reference X-ray beam 1001 detected by the light detector 1005. The intensity of light emitted from the scintillator 1006 by the incident X-ray beam 1002 refracted at the test object 104 detected by the light detector 1010 is represented by Expression 11. The displacement $\Delta x$ on the scintillator 1006 can be determined from Expressions 10 and 11 using Expression 12. The X-ray transmittance A of the test object 104 can be determined from the intensity ratio of the reference X-ray beam 1007 at the optical filter 1009 to the refracted X-ray beam 1008. By determining the X-ray transmittance A, minute displacement due to refraction of the test object 104 can be determined from the relationship between the detected intensities of the reference X-ray beam 1001 and the X-ray beam 1002.

In such a case, since information about light intensity in two different areas, i.e., the optical filter 1004 and the optical filter 1009, is used, the spatial resolution in the x direction is reduced to one-half. To prevent the decrease in spatial resolution, it is also possible to perform a similar measurement by moving the splitting element 103 and the detecting unit 105 or the test object 104 in the X direction by a length equal to the optical filter 1004 in the X direction.

In this way, information about the X-ray transmittance A corresponding to the position of the test object 104 of which the X-ray displacement has been measured can be acquired.

The displacement Δx and the X-ray transmittance A may be determined by referring to a data table, which is stored in the computing unit 106 and contains the correspondence relationship between the intensity of light detected when the test object 104 is not disposed and the position x inside the light detector 1005. The flow chart of the computing unit 106 is the same as that of the third embodiment. With the above-described configuration, displacement images, differential phase contrast images, and phase contrast images that take into consideration absorption can be acquired.

Eighth Embodiment

Configuration Without Splitting Element

In the eighth embodiment, an X-ray imaging apparatus that acquires an image from X-ray phase shift will be described. In this embodiment, different from the embodiments described above, a splitting element is not included.

Figure 11:
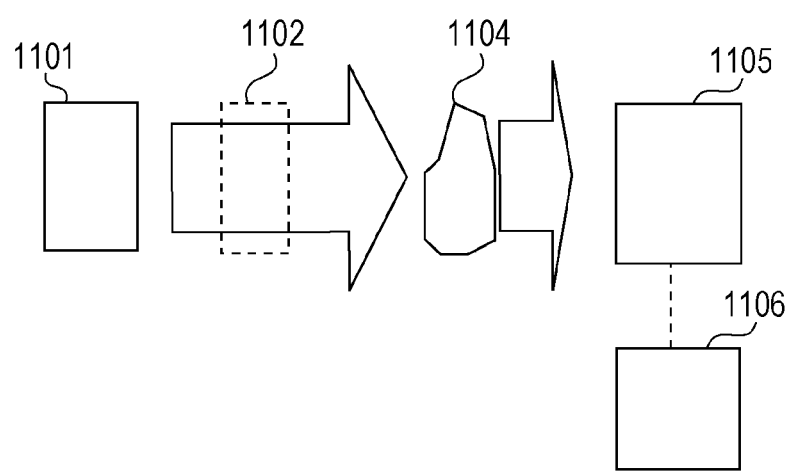
FIG. 11 is a schematic view of an X-ray imaging apparatus according to an eighth embodiment of the present invention.

FIG. 11 illustrates an X-ray imaging apparatus according to this embodiment. FIG. 11 illustrates an X-ray source 1101, a monochromatizing unit 1102, a test object 1104, a detecting unit 1105, and a display unit 1106.

The phase of an X-ray beam emitted from the X-ray source 1101 shifts at the test object 1104. As a result, the X-ray beam is refracted. The refracted X-ray beam is incident on the detecting unit 1105.

The detecting unit 1105 may include the light-attenuating unit of the first embodiment or the light-shielding unit of the second embodiment. It is also possible to use units according to other embodiments.

Information about an X-ray beam acquired by the detecting unit 1105 is output to the display unit 1006. When a monochromatic X-ray is used, the monochromatizing unit 1102 may be disposed between the X-ray source 1101 and the test object 1104.

Figure 12:
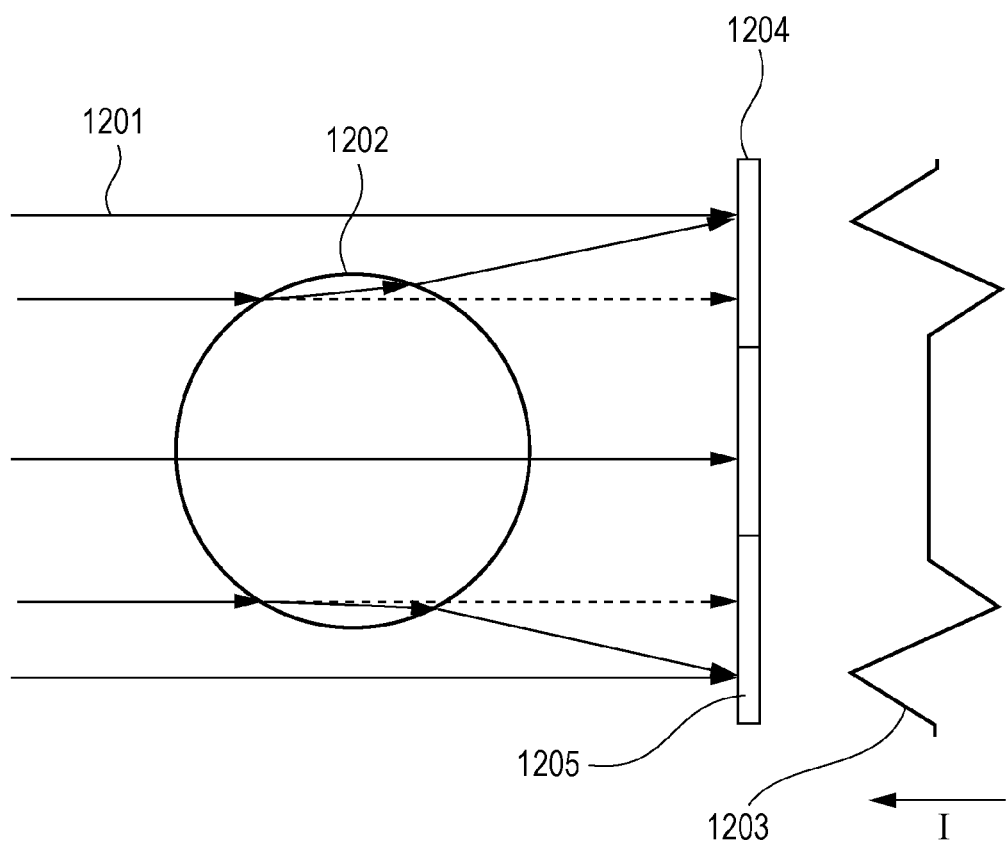
FIG. 12 illustrates an X-ray beam being refracted at an object.

FIG. 12 is a schematic view of refraction of an X-ray beam transmitted through an object. Since the refractive index of the X-ray with respect to the object is slightly smaller than one, when an X-ray beam is incident on an object 1202 in such a manner illustrated in FIG. 12, for example, an X-ray beam 1201 incident on an area at the border between the object 1202 and the surroundings is refracted outward. At this time, as represented by transmitted-X-ray intensity distribution 1203, the intensities of the transmitted X-ray beam refracted at the border area of the object and the X-ray beam that has traveled the outside of the object strengthen each other. In the section on the extended line from the incident point of the refracted X-ray beam on the object, the X-ray beams become weak.

As a result, the acquired transmitted-X-ray intensity distribution 1203 has a distribution in which the outline of the object 1202 is emphasized. However, since the refractive angle of the X-ray beam is very small, in consideration of the pixel size of the detector, such an emphasized outline cannot be detected unless the object and the detector are disposed at a sufficient distance.

When this distance is decreased, the strengthening and weakening of X-ray beams as described above occur inside a single pixel 1205 of a detector 1204, causing the X-ray beams to be cancelled out. Thus, an image with an emphasized outline cannot be acquired.

Accordingly, in this embodiment, the detecting unit 1105 that detects the strengthening and weakening of X-ray beams even when the distance between an object and the detector is small is used. Next, the detecting unit 1105 will be described.

Figure 13:
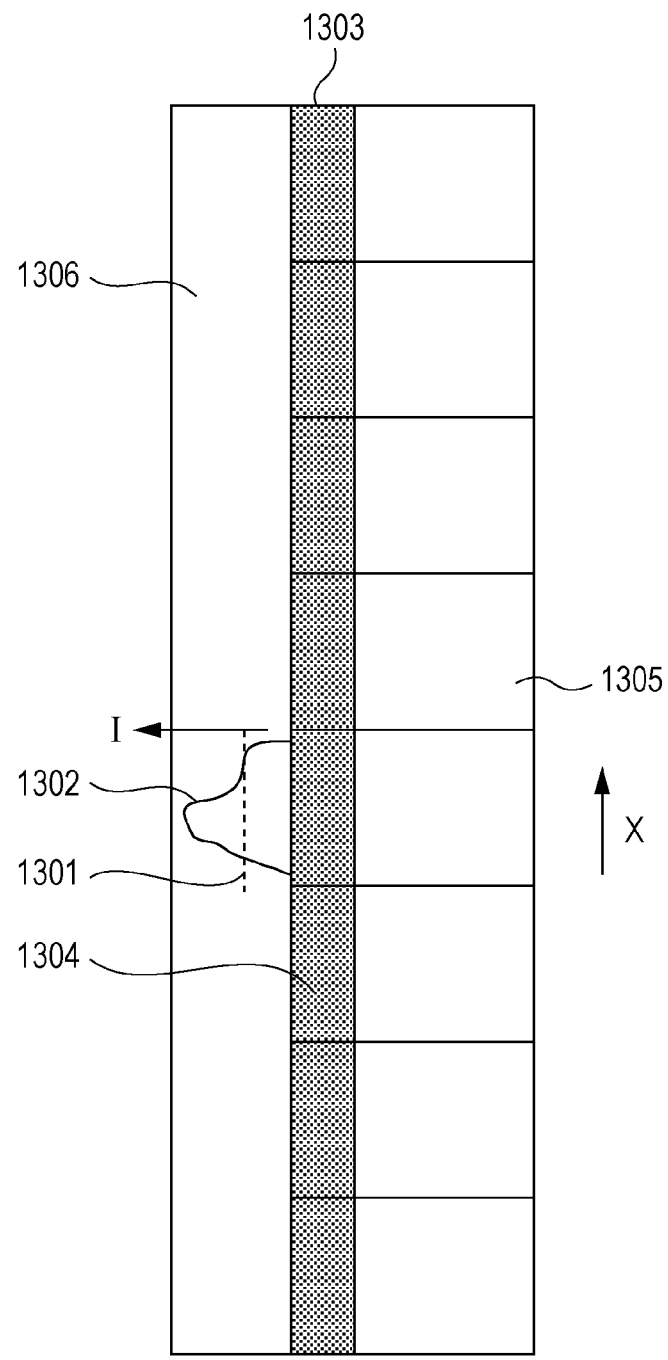
FIG. 13 is a schematic view of a detecting unit according to the eighth embodiment of the present invention.

FIG. 13 is a schematic view of part of the detecting unit 1105. The detecting unit 1105 includes a scintillator 1306, a light-attenuating unit 1303, and a light detector 1305. The light-attenuating unit 1303 includes two-dimensionally arranged optical filters 1304. Each of the optical filters 1304 has a transmittance gradient in which the transmittance of the light emitted from the scintillator 1306 continuously changes in the X direction. A reference-X-ray intensity distribution 1301 represents an intensity distribution of an X-ray beam incident on the scintillator 1306 in an area of a single optical filter 1304 when the test object 1104 is not disposed. The distribution is uniform.

An X-ray intensity distribution 1302 represents an intensity distribution of an X-ray beam incident on the scintillator 1306, which has changed due to refraction by the test object 1104. The integrated intensity of these distributions when the test object 1104 substantially does not absorb X-rays is the same. In other words, when the optical filters 1304 are not provided, the same intensity is detected.

In contrast, by disposing the optical filters 1304 of which the transmitted X-ray intensities change in the X direction, the intensity distribution change due to X-ray refraction at the test object 1104 can be converted to a change in the transmitted X-ray intensity.

Since only a change in the intensity distribution can be extracted through division by an image captured when the test object 1104 is not disposed, minute refraction can be detected as an X-ray intensity distribution.

The test object 1104 having sufficient X-ray absorption affects the change in the intensity distribution. However, this is not a problem from the viewpoint of visualization of the test object 1104.

Optical filters having sensitivity to displacement in the X and Y directions can also be used. In this way, it is possible to detect a phase gradient in the two-dimensional direction.

By stacking an optical filter having a transmittance gradient in the X direction and an optical filter having a transmittance gradient in the Y direction, a phase gradient in the two-dimensional direction can be detected.

With such a configuration, since a minute change in intensity distribution can be detected, the distance between the test object 1104 and the detecting unit 1105 does not have to be set large, and thus the size of the apparatus can be reduced. When the distance between the test object 1104 and the detecting unit 1105 is set large, a change in the intensity distribution due to minute refraction can also be detected. X-ray beams with high interference are not necessarily required to utilize X-ray refraction in phase shift detection, and it is possible to acquire an image as a result of the refraction of the X-ray beam at the test object by using such an X-ray imaging apparatus.

An X-ray shielding mask using heavy elements that block X-rays are not required.

As described above, the light-attenuating unit 1303 is used in the detecting unit 1105. Instead of the light-attenuating unit 1303, a light-shielding unit may be used to achieve the same effect.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010 -019448, filed Jan. 29, 2010 and No. 2010 -159886 filed Jul. 14, 2010, which are hereby incorporated by reference herein in their entirety.

REFERENCE SIGNS LIST

101 X-ray source
102 monochromatizing unit
103 splitting element
104 test object
105 detecting unit
106 computing unit
107 display unit
201 reference X-ray beam
202 X-ray beam
203 light-shielding unit
204 optical filter
205 light detector
206 scintillator

The invention claimed is:

1. An X-ray imaging apparatus comprising:
a splitting element configured to spatially divide an X-ray emitted from an X-ray source;
a scintillator configured to emit light when a divided X-ray beam divided at the splitting element is incident on the scintillator;
a light-transmission limiting unit configured to limit transmitting amount of the light emitted from the scintillator; and
a plurality of light detectors each configured to detect the amount of light that has transmitted through the light-transmission limiting unit,
wherein the light-transmission limiting unit is configured such that a light intensity detected at each of the light detectors changes in response to a change in an incident position of the X-ray beam.

2. The X-ray imaging apparatus according to claim 1,
wherein the light-transmission limiting unit comprises a light-attenuating unit configured to attenuate the light emitted from the scintillator, and
wherein the light-attenuating unit comprises a plurality of optical filters each configured to continuously change detected amounts of light intensity in response to the incident position of the X-ray beam.

3. X-ray imaging apparatus according to claim 2, wherein each of the optical filters is configured such that detected amounts of light intensity in a direction orthogonal to the incident X-ray beam changes.

4. The X-ray imaging apparatus according to claim 1,
wherein the light-transmission limiting unit comprises a light-shielding unit configured to block the light emitted from the scintillator, and
wherein the light-shielding unit comprises a plurality of light-shielding masks each configured to block part of the light emitted from the scintillator.

5. The X-ray imaging apparatus according to claim 4, wherein the light-shielding masks are disposed on borders between the optical detectors.

6. The X-ray imaging apparatus according to claim 4,
wherein the light-shielding unit comprises two different types of light-shielding masks having different detected amounts of light intensity changes per unit distance when the incident position of the X-ray beam is moved in a predetermined direction, and
wherein the two different types of light-shielding masks adjoin each other.

7. The X-ray imaging apparatus according to claim 4,
wherein the light-shielding unit includes a first area containing a first light-shielding mask configured such that the light intensity detected at the optical detector increases when the incident position of the X-ray beam moves in a predetermined direction and a second area containing a second light-shielding mask configured such that the light intensity detected at the optical detector decreases when the incident position of the X-ray beam moves in a predetermined direction, and
wherein the first area and the second area adjoin each other.

8. The X-ray imaging apparatus according to claim 4,
wherein the light-shielding unit includes a first area containing the light-shielding mask and a second area containing no light-shielding mask, and
wherein the first area and the second area adjoin each other.

9. The X-ray imaging apparatus according to claim 4, wherein an area containing a light-shielding mask and an area not containing a light-shielding mask are disposed on borders of the light detectors.

10. The X-ray imaging apparatus according to claim 2,
wherein the light-attenuating unit comprises two different types of optical filters having different detected amounts of light intensity changes per unit distance when the incident position of the X-ray beam is moved in a predetermined direction, and
wherein the two different types of optical filters adjoin each other.

11. The X-ray imaging apparatus according to claim 2,
wherein the light-attenuating unit includes a first area containing a first optical filter configured such that the light intensity detected at the optical detector increases when the incident position of the X-ray beam moves in a predetermined direction and a second area containing a second optical filter configured such that the light intensity detected at the optical detector decreases when the incident position of the X-ray beam moves in a predetermined direction, and
wherein the first area and the second area adjoin each other.

12. The X-ray imaging apparatus according to claim 2,
wherein the light-attenuating unit includes a first area containing the optical filter and a second area not containing the optical filter, and
wherein the first area and the second area adjoin each other.

13. The X-ray imaging apparatus according to claim 1, further comprising:
a computing unit configured to compute an image associated with a phase shift of the X-ray beam on the test object from light intensity detected by the detecting unit.

14. A method of X-ray imaging comprising the steps of:
spatially dividing an X-ray emitted from an X-ray source;
emitting light when the spatially divided X-ray beam is incident on the scintillator; and
acquiring information about a phase shift of the X-ray beam due to a test object using a light-transmission limiting unit configured such that a light intensity detected at each of the light detectors changes in response to a change in an incident position of the X-ray beam.

15. An X-ray imaging apparatus comprising:
a scintillator configured to emit light when the X-ray beam is incident on the scintillator;
a light-transmission limiting unit configured to limit transmitting amount of the light emitted from the scintillator in the response to a change in X-ray intensity distribution that occur when an X-ray beam is transmitted through a test object; and
a plurality of light detectors each configured to detect the amount of light that has transmitted through the light-transmission limiting unit.

16. A method of X-ray imaging comprising the steps of:
emitting light when the X-ray beam is incident on the scintillator; and
detecting the amount of light that has transmitted through the light-transmission limiting unit, wherein the light-transmission limiting unit is configured such that a light intensity detected at each of the light detectors changes in response to a change in X-ray intensity distribution that occur when an X-ray beam is transmitted through a test object.

* * * * *